(12) United States Patent
Bermudez Rodriguez et al.

(10) Patent No.: US 10,247,687 B2
(45) Date of Patent: Apr. 2, 2019

(54) SOIL MOISTURE PROBING AT VARIABLE DEPTH

(71) Applicant: INTERNATIONAL BUSINESS MACHINES CORPORATION, Armonk, NY (US)

(72) Inventors: Sergio A. Bermudez Rodriguez, Boston, MA (US); Hendrik F. Hamann, Yorktown Heights, NY (US); Levente Klein, Tuckahoe, NY (US); Michael A. Schappert, Wappingers Falls, NY (US); Theodore G. van Kessel, Millbrook, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 465 days.

(21) Appl. No.: 15/058,970

(22) Filed: Mar. 2, 2016

(65) Prior Publication Data
US 2017/0254766 A1  Sep. 7, 2017

(51) Int. Cl.
| | |
|---|---|
| *G05B 1/00* | (2006.01) |
| *G01N 27/04* | (2006.01) |
| *G01N 33/24* | (2006.01) |
| *G01N 27/30* | (2006.01) |
| *G01N 27/333* | (2006.01) |
| *A01G 2/00* | (2018.01) |

(52) U.S. Cl.
CPC ......... *G01N 27/048* (2013.01); *G01N 27/301* (2013.01); *G01N 27/333* (2013.01); *G01N 33/246* (2013.01); *A01G 2/00* (2018.02); *G05B 1/00* (2013.01); *G05B 2219/00* (2013.01)

(58) Field of Classification Search
CPC ........ A01G 2/00; G05B 1/00; G05B 2219/00; G01N 1/00; G01N 2201/00
See application file for complete search history.

(56) References Cited

U.S. PATENT DOCUMENTS

| | | |
|---|---|---|
| 4,655,076 A | 4/1987 | Weihe et al. |
| 5,570,030 A | 10/1996 | Wightman |
| | (Continued) | |

OTHER PUBLICATIONS

Baumhardt, R.L., et al., Soil Material, Temperature, and Salinity Effects on Calibration of Multisensor Capacitance Probes, Soil Sci. Soc. Am. J., Nov.-Dec. 2000, pp. 19401946.

(Continued)

*Primary Examiner* — Jermele M Hollington
*Assistant Examiner* — Temilade Rhodes-Vivour
(74) *Attorney, Agent, or Firm* — Tutunjian & Bitetto, P.C.; Vazken Alexanian

(57) ABSTRACT

A soil moisture sensor and a soil moisture sensing system are provided. The soil moisture sensor includes a double groove helical structure having grooves and formed from an insulator. The soil moisture sensor further includes at least a first electrode and a second electrode formed from one or more metals deposited at at least two different locations on the grooves. The soil moisture sensor also includes a processor for processing a soil moisture measurement signal based on a conductivity between the electrodes. The soil moisture sensor additionally includes a wireless transmitter for transmitting the soil moisture measurement signal to a remote location.

20 Claims, 8 Drawing Sheets

(56) References Cited

U.S. PATENT DOCUMENTS

| | | | |
|---|---|---|---|
| 6,242,927 | B1 | 6/2001 | Adams et al. |
| 6,441,622 | B1 | 8/2002 | Wrzesinski et al. |
| 7,487,925 | B2 * | 2/2009 | Skinner ................ A01G 17/02 239/63 |
| 8,915,131 | B2 | 12/2014 | Aughton et al. |
| 8,947,102 | B1 | 2/2015 | Evett et al. |
| 2005/0087620 | A1 * | 4/2005 | Bowers ................ A01G 25/167 239/63 |
| 2011/0035059 | A1 * | 2/2011 | Ersavas ................ A01G 25/167 700/276 |
| 2011/0273196 | A1 * | 11/2011 | Hill .................... A01G 25/167 324/696 |
| 2014/0252103 | A1 * | 9/2014 | Hamann ................ B05B 12/04 239/1 |
| 2016/0183484 | A1 * | 6/2016 | Richings, Sr. ....... A01G 25/167 239/11 |

OTHER PUBLICATIONS

Fares, A., et al., "Advances in Crop Water Management Using Capacitive Water Sensors", Advances in Agronomy, Elsevier Inc., Dec., 2006, pp. 43-77, vol. 90.

Holler, M., "High density, Multiple Depth, Wireless Soil Moisture Tension Measurements for Irrigation Management", Am. Soc. For Enology and Viticulture, Jun. 2008, 8 pages.

* cited by examiner

SOIL MOISTURE PROBING AT VARIABLE DEPTH

BACKGROUND

Technical Field

The present invention relates generally to irrigation and, in particular, to soil moisture probing at variable depth.

Description of the Related Art

Soil moisture measurements are required to determine the amount of water to be used for irrigation. To obtain reliable soil moisture measurements, soil moisture sensors are buried in the ground. In many cases, the soil moisture sensors can be brittle and require significant work in order to be inserted in the ground. Moreover, such soil moisture sensors require a reliable contact between the electrodes and the soil. Such insertion will require digging a hole and then allowing the soil to settle in order for the sensor to make good contact with the soil. Thus, the contact will not be reliable until the ground has settled. Due to the digging and/or shoveling, the soil is disturbed and the resultant measurement may not reflect the profile that may be encountered in undisturbed places where the ground was set through years. Furthermore, measuring moisture at different depths requires the insertion of individual sensors that may require separate processing and signal conditioning. Thus, there is a need for an improved way to make soil measurements at varying depths.

SUMMARY

According to an aspect of the present principles, a soil moisture sensor is provided. The soil moisture sensor includes a double groove helical structure having grooves and formed from an insulator. The soil moisture sensor further includes at least a first electrode and a second electrode formed from one or more metals deposited at at least two different locations on the grooves. The soil moisture sensor also includes a processor for processing a soil moisture measurement signal based on a conductivity between the electrodes. The soil moisture sensor additionally includes a wireless transmitter for transmitting the soil moisture measurement signal to a remote location.

According to another aspect of the present principles, a soil moisture sensing system is provided. The soil moisture sensing system includes a plurality of soil moisture sensors. Each of the soil moisture sensors includes a double groove helical structure having grooves and formed from an insulator. Each of the soil moisture sensors further includes at least a first electrode and a second electrode formed from one or more metals deposited at at least two different locations on the grooves. Each of the soil moisture sensors also includes a processor for processing a soil moisture measurement signal based on a conductivity between the electrodes. Each of the soil moisture sensors additionally includes a wireless transmitter for transmitting the soil moisture measurement signal. The soil moisture sensing system further includes a wireless receiver for receiving the soil moisture measurement signal at a remote location.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

The present principles are directed to soil moisture probing at variable depth.

In an embodiment, the present principles provide customized sensors that can have a shape and form that is designed to overcome the mechanical resistance of the typical soil profile encountered in a farm and allow the sensor to be inserted into the ground with minimal effort. The sensor can be fabricated using simple techniques like a three-dimensional (3D) printer or can be machine fabricated, extruded, and so forth. In an embodiment, the electrodes are located inside the groves of a double drill bit. In an embodiment, the double drill bit is fabricated from plastic. However, other materials can also be used, while maintaining the spirit of the present principles.

Advantageously, a moisture sensor in accordance with the present principles overcomes at the aforementioned deficiencies of the prior art, and can probe moisture at different depths and calculate the soil moisture using a microcontroller. A signal indicative of the soil moisture can be easily transmitted using a wireless radio network.

Figure 1:
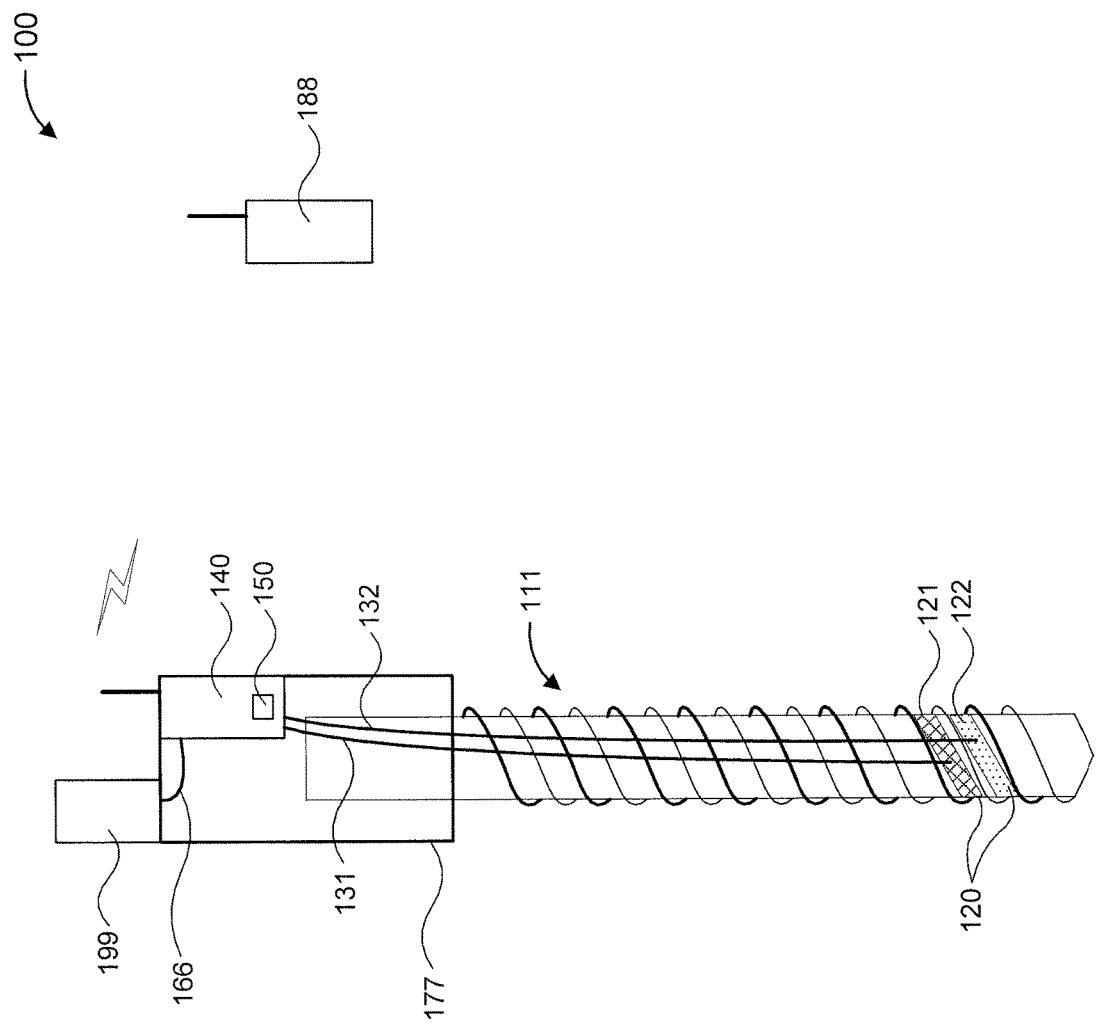
FIG. 1 shows an exemplary soil moisture sensor 100 having a pair of soil moisture sensing electrodes, in accordance with an embodiment of the present principles.

FIG. 1 shows an exemplary soil moisture sensor 100 having a pair of soil moisture sensing electrodes, in accordance with an embodiment of the present principles.

The sensor 100 includes a double groove helical structure 110 where one or more metals 120 are deposited in the grooves 111 of the double groove helical structure 110 such that the one or more metals 120 form two electrodes 121, 122 that are electrically separated. Electrode 121 is shown using a cross-hatched pattern, while electrode 122 is shown using a dotted hatch pattern. The grooves 111 can be plated with different metals, for example, chosen for their corrosion resistance and/or their electrochemical potential.

The body of the helical structure 110 can be plastic (or made from some other non-conducting material(s)) in order to electrically isolate the two electrodes 121, 122.

In soils that have some moisture, a finite conductivity is measured between the two electrodes 121, 122. The conductivity between the two electrodes 121, 122 is an indicator of the soil moisture level. For example, no moisture results in large resistance, while a moisture level will lower the resistance until it reach the conductance of water (which will be the signal expected during heavy rains). The galvanic current level is an indicator of the soil moisture level.

The one or more metals 120 deposited in the grooves 111 (i.e., electrodes 121, 122) can be connected to the wireless radio 140 (situated above ground) with two sets of wires (also interchangeably referred to as "connectors") 131, 132. The two sets of wires 131, 132 carry power to the electrodes and carry measurement signals from the electrodes.

The resultant signal is processed onboard by a processor 150, with periodic reporting on the soil moisture level to, for example, a receiver 188 at a local or remote location. Hence, the wireless radio 140 can be any device capable of wireless communication and having a processor for performing specific programmed tasks/functions in order to determine the soil moisture level based on the conductivity between the electrodes. In another embodiment, a separate data processing device can be used (as shown and described with respect to the sensor 200 of FIG. 2).

Due to the helical shape, the sensor 100 can be easily inserted into the ground and if required can be removed and reinserted quickly, thereby avoiding the hassle of digging a new hole in the ground. Moreover, the sensor 100 can be inserted at any depth if only one pair of electrodes is used.

The sensor 100 can be powered using any applicable power source 199, as readily appreciated by one of ordinary skill in the art given the teachings of the present principles provided herein. In an embodiment, for example, a battery and/or a solar panel can be used to power the sensor 100. A connector 166 (e.g., one or more wires, a bus, etc.) connects the power source 199 to the wireless radio 140 and the processor 150.

The double groove helical structure 110 essentially forms a drill bit. The double groove helical structure 110 can be fabricated using, for example, a 3D printer, an injection mold, and/or any other suitable plastic fabrication mechanism, as readily appreciated by one of ordinary skill in the art.

An enclosure 177, attached to the top of the double groove helical structure 110, includes the radio 140 (with processor 150), connector 166, portions of the connectors 131, 132, and possibly portions of the power source 199.

Multiple electrode bands (electrode pairs) can be deposited at different locations along the helical structure to enable moisture measurements at different depths. The sensing at different depths can detect the propagation speed of water into the soil. The water will first reach the first sensor at a first depth and create a signal, then the water will reach the second sensor at a second depth at a later moment and will reach a third sensor at a third depth at a further moment of time. The time differences when the soil moisture sensors detect the water can be related to change in the water penetration into the soil. An implementation of the use of multiple electrode bands is shown and described with respect to FIG. 2.

Figure 2:
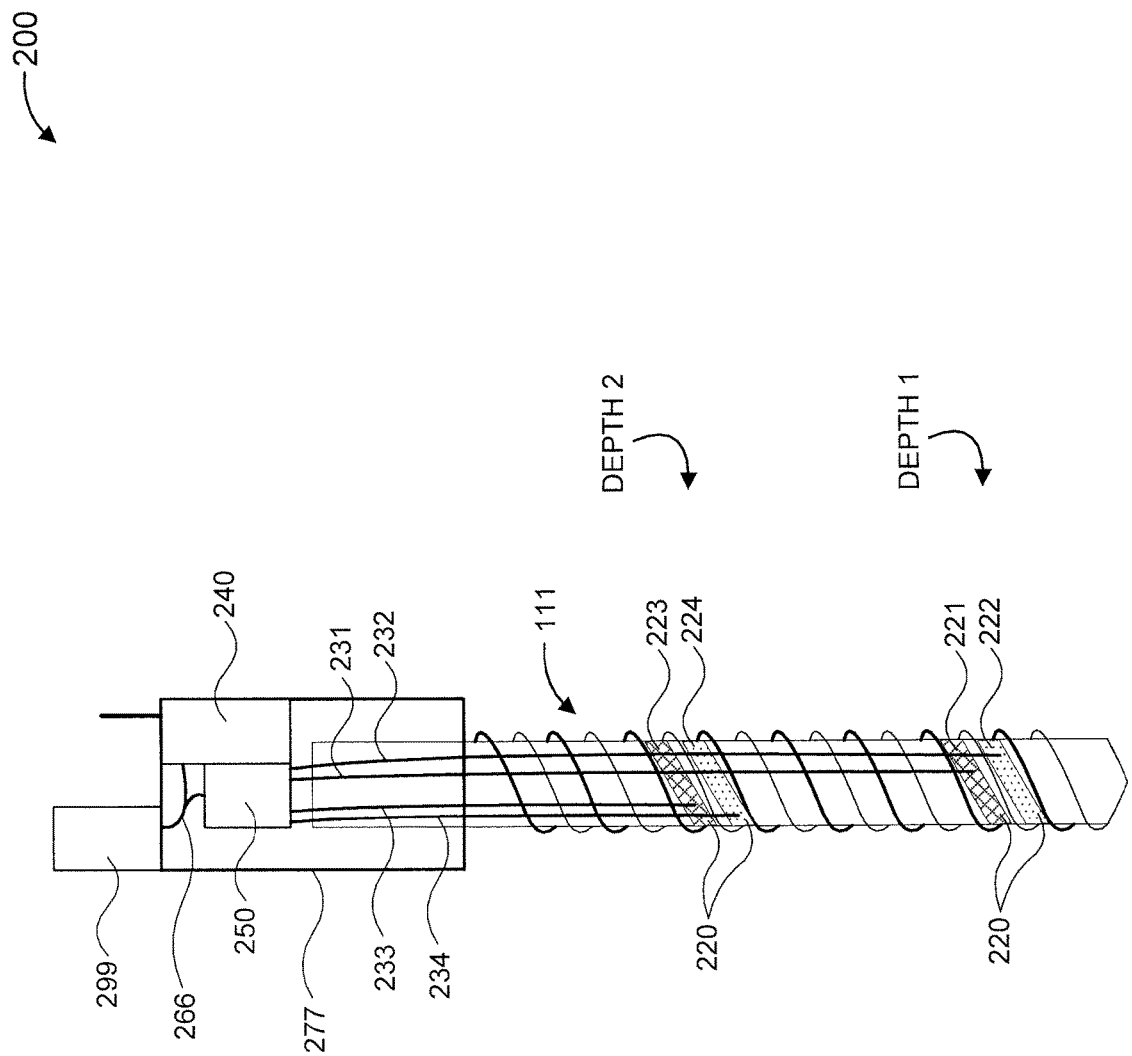
FIG. 2 shows an exemplary soil moisture sensor 200 having multiple pairs of soil moisture sensing electrodes at different depths, in accordance with an embodiment of the present principles.

FIG. 2 shows an exemplary soil moisture sensor 200 having multiple pairs of soil moisture sensing electrodes at different depths, in accordance with an embodiment of the present principles.

The sensor 200 includes a double groove helical structure 210 where one or more metals 220 are deposited in the grooves 211 of the double groove helical structure 210 such that the one or more metals 220 form two electrode pairs 221, 222 and 223, 224. Electrodes 221 and 223 are shown using a cross-hatched pattern, while electrodes 222 and 224 is shown using a dotted hatch pattern. The grooves 211 can be plated with different metals, for example, chosen for their corrosion resistance and/or their electrochemical potential.

In the embodiment of FIG. 2, the two electrode pairs 221, 222 and 223, 224 are at different depths along the double groove helical structure 210 in order to provide different soil moisture measurements at the different depths (i.e., depth 1 and depth 2).

The electrodes in each pair are electrically separated from each other, and each of the pairs are electrically separated from each other. The body of the helical structure 210 can be plastic (or made from some other non-conducting material(s)) in order to electrically isolate the electrodes.

The one or more metals 220 deposited in the grooves 211 can be connected with four sets of wires 231, 232 and 233, 234. The four sets of wires 231, 232, 233, 234 carry power to the electrodes and carry measurement signals from the electrodes.

In the embodiment of FIG. 2, a data processing unit 250 is used. Data processing unit 250 is a separate element from wireless radio 240 and is connected to wireless radio 240 in order to provide an output signal to the wireless radio 240 for transmission to a remote location/device.

A power source 299 powers the sensor 200. In an embodiment, for example, a battery and/or a solar panel can be used to power the sensor 200. A connector 266 (e.g., one or more wires, a bus, etc.) connects the power source 299 to the wireless radio 240 and the processor 250.

An enclosure 277, attached to the top of the double groove helical structure 210, includes the radio 240, the processor 250, connector 266, portions of the connectors 231, 232, 233, 234, and possibly portions of the power source 299.

Figure 3:
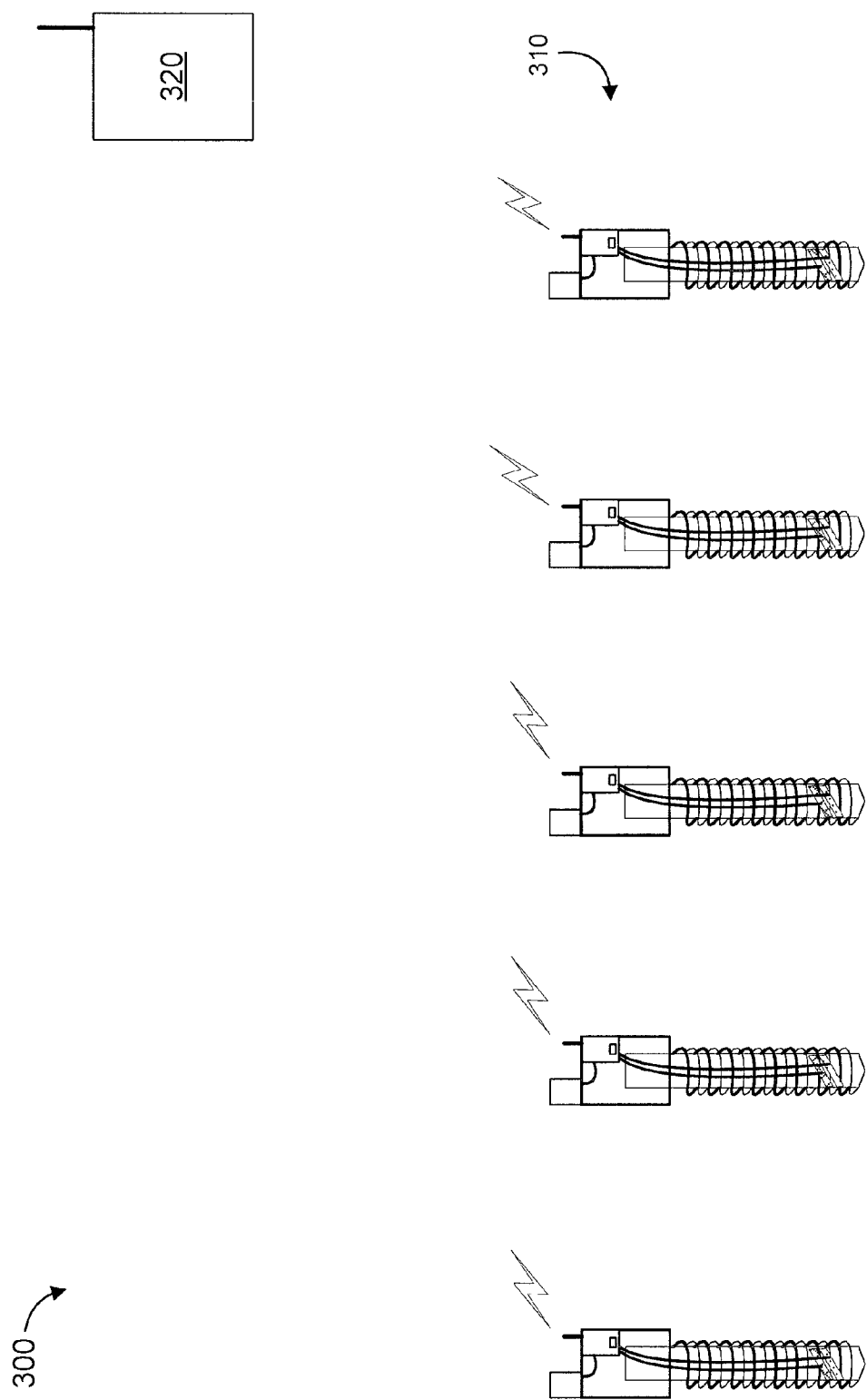
FIG. 3 shows an exemplary system 300 for soil moisture sensing, in accordance with an embodiment of the present principles.

FIG. 3 shows an exemplary system 300 for soil moisture sensing, in accordance with an embodiment of the present principles.

The system 300 includes multiple soil moisture sensors 310. Each of the sensors 310 can be implemented by sensor 100 in FIG. 1 and/or sensor 200 in FIG. 2. Each of the sensors 310 can form a mote in a sensor network implemented as system 300.

Each of the multiple soil moisture sensors 310 report to a central monitoring device 320. The central monitoring device 320 can be implemented as a server, a tablet, a smart phone (cellular and/or WIFI), a laptop computer, a desktop computer, a personal digital assistance, a multimedia player, and so forth. Basically, any device that can wireless receive data can be used.

In an embodiment, aggregated data can be used by the central monitoring device 320 to create time dependent soil moisture maps at different depths.

Figure 4:
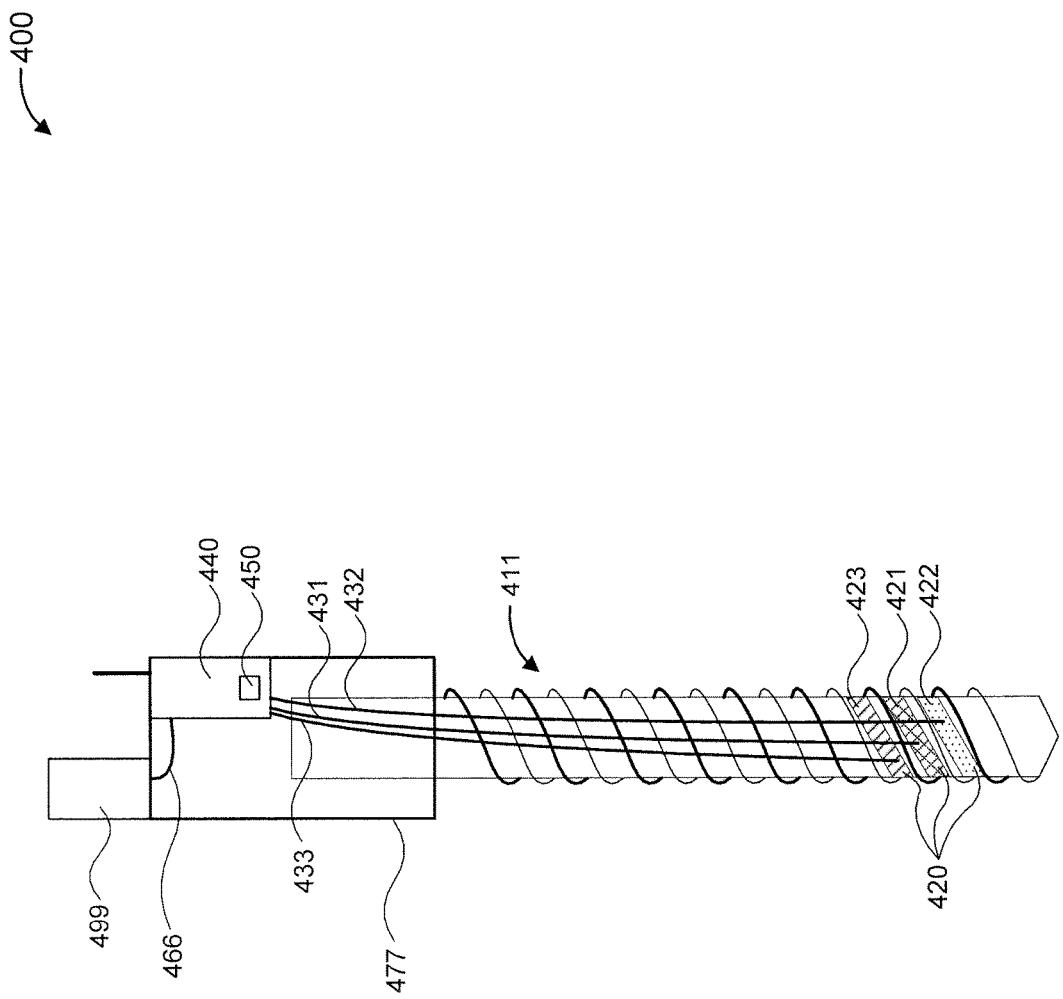
FIG. 4 shows an exemplary soil moisture sensor 400 having three electrodes, in accordance with an embodiment of the present principles.

FIG. 4 shows an exemplary soil moisture sensor 500 having three electrodes, in accordance with an embodiment of the present principles.

The soil moisture sensor 400 includes 3 electrodes per band, with one band shown in the embodiment of FIG. 4. That is, soil moisture sensor 400 includes electrodes 421, 422, 423. Electrode 423 is configured as a reference electrode for three electrode electrochemical measurements. Electrode 421 is shown using a cross-hatched pattern, electrode 422 is shown using a dotted hatch pattern, and electrode 423 is shown using a diagonal line hatch pattern.

In an embodiment, the sensor body and the material can be deposited using the 3D printer where for the body plastic material is used, while for electrodes metals can be used. The shape and size of the sensor can be adjusted on the fly based on the soil composition, mechanical strength and depth to a rock that restrict sensor penetration.

The electrodes 421, 422, 423 are formed from one or more metals 420 deposited in the grooves 411, and can be connected to the wireless radio 440 with three sets of wires (also interchangeably referred to as "connectors") 431, 432, 433. The three sets of wires 431, 432, 433 carry power to the electrodes and carry measurement signals from the electrodes. The resultant signal is processed onboard by a processor 450, with periodic reporting on the soil moisture level to, for example, a receiver at a local or remote location. Hence, the wireless radio 440 can be any device capable of wireless communication and having a processor for performing specific programmed tasks/functions in order to determine the soil moisture level based on the conductivity between the electrodes. In another embodiment, a separate data processing device can be used (as shown and described with respect to the sensor 200 of FIG. 2).

A power source 499 powers the sensor 400. In an embodiment, for example, a battery and/or a solar panel can be used to power the sensor 400. A connector 466 (e.g., one or more wires, a bus, etc.) connects the power source 499 to the wireless radio 440 and the processor 450.

An enclosure 477, attached to the top of the double groove helical structure 410, includes the radio 440 (with processor 450), connector 466, portions of the connectors 431, 432, 433, and possibly portions of the power source 499.

In another embodiment, a soil moisture sensor in accordance with the present principles can have multiple bands with 3 electrodes per band, or can have at least one 3 electrode band and at least other band with a different number of electrodes (e.g., two, four).

Figure 5:
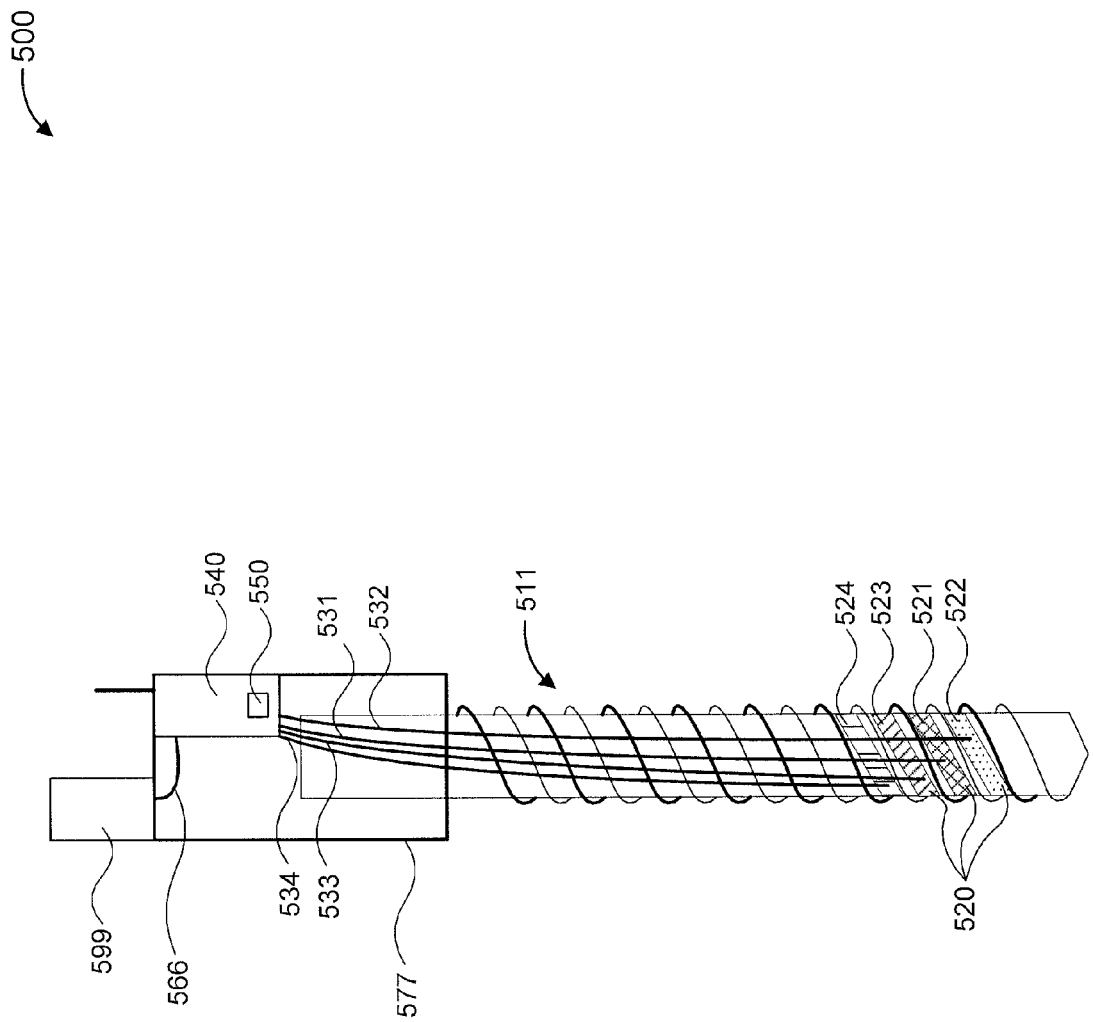
FIG. 5 shows an exemplary soil moisture sensor 500 having four electrodes, in accordance with an embodiment of the present principles.

FIG. 5 shows an exemplary soil moisture sensor 500 having four electrodes, in accordance with an embodiment of the present principles.

The soil moisture sensor 500 includes 4 electrodes per band, with one band shown in the embodiment of FIG. 5. That is, soil moisture sensor 500 includes electrodes 521, 522, 523, 524. Electrode 523 is configured as a reference electrode and electrode 524 is configured as a sense electrode, for four electrode electrochemical measurements. Electrode 521 is shown using a cross-hatched pattern, electrode 522 is shown using a dotted hatch pattern, electrode 523 is shown using a diagonal line hatch pattern, and electrode 524 is shown using a vertical line hatch pattern.

The electrodes 521, 522, 523, 524 are formed from one or more metals 520 deposited in the grooves 511, and can be connected to the wireless radio 540 with four sets of wires (also interchangeably referred to as "connectors") 531, 532, 533, 534. The four sets of wires 531, 532, 533, 534 carry power to the electrodes and carry measurement signals from the electrodes. The resultant signal is processed onboard by a processor 550, with periodic reporting on the soil moisture level to, for example, a receiver at a local or remote location. Hence, the wireless radio 540 can be any device capable of wireless communication and having a processor for performing specific programmed tasks/functions in order to determine the soil moisture level based on the conductivity between the electrodes. In another embodiment, a separate data processing device can be used (as shown and described with respect to the sensor 200 of FIG. 2).

A power source 599 powers the sensor 500. In an embodiment, for example, a battery and/or a solar panel can be used to power the sensor 500. A connector 566 (e.g., one or more wires, a bus, etc.) connects the power source 599 to the wireless radio 540 and the processor 550.

An enclosure 577, attached to the top of the double groove helical structure 510, includes the radio 540 (with processor 550), connector 566, portions of the connectors 531, 532, 533, 534, and possibly portions of the power source 599.

In another embodiment, a soil moisture sensor in accordance with the present principles can have multiple bands with 4 electrodes per band, or can have at least one 4 electrode band and at least other band with a different number of electrodes (e.g., two, three).

Figure 6:
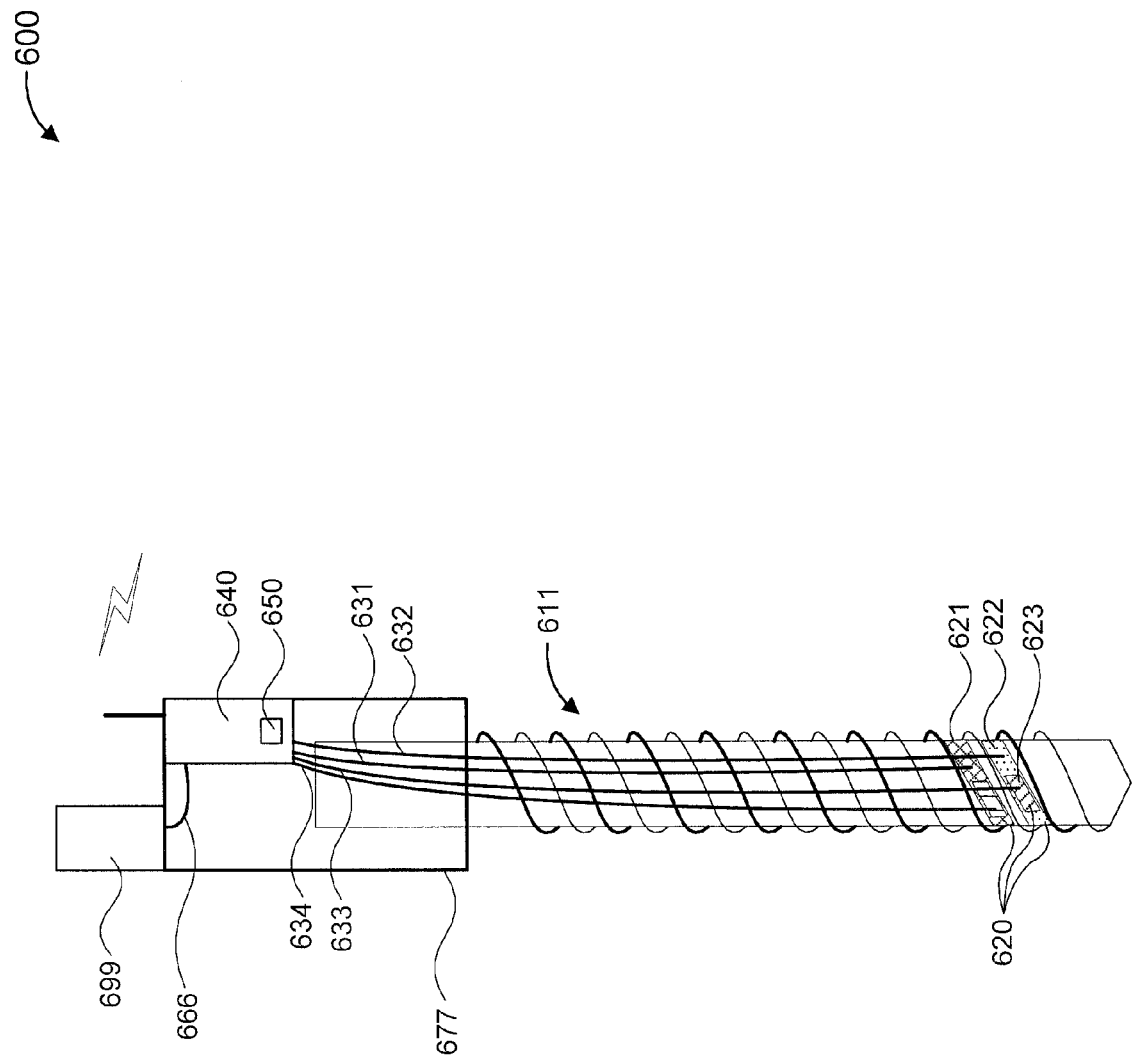
FIG. 6 shows an exemplary soil moisture sensor 600 having a pair of soil moisture sensing electrodes and a pair of ion-selective electrodes, in accordance with an embodiment of the present principles.

FIG. 6 shows an exemplary soil moisture sensor 600 having a pair of soil moisture sensing electrodes and a pair of ion-selective electrodes, in accordance with an embodiment of the present principles.

The soil moisture sensor 600 includes two electrodes (621, 622) for conductivity measurements and two ion-selective electrodes 623, 624. That is, soil moisture sensor 600 includes electrodes 621, 622, 623, 624. Electrode 621 is shown using a cross-hatched pattern, electrode 622 is shown using a dotted hatch pattern, electrode 623 is shown using a diagonal line hatch pattern, and electrode 624 is shown using a vertical line hatch pattern. Electrode 623 can serve as a sense electrode and electrode 624 can serve as a reference electrode.

The pair of ion-selective electrodes 623, 724 is deposited on the top of metal (here, on top of electrode 621 and on top of electrode 622) for measuring micro-nutrients in the soil. Such micronutrients that can be measured include, but are not limited to, nitrogen, potassium, and phosphorus. The sensor rely on ion selective electrodes that change potential based on the nutrients in the soil. The ion selective electrodes are transducers (sensors) that convert the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The voltage detected on the electrode is dependent on the type of nutrients that need to be detected and multiple ion selective material can be deposited on the same probe to extract information about soil moisture and existing nutrients in the soil.

The electrodes 621, 622, 623, 624 are formed from one or more metals 620 deposited in the grooves 611, and can be connected to the wireless radio 640 with four sets of wires (also interchangeably referred to as "connectors") 631, 632, 633, 634. The four sets of wires 631, 632, 633, 634 carry power to the electrodes and carry measurement signals from the electrodes. The resultant signal is processed onboard by a processor 650, with periodic reporting on the soil moisture level to, for example, a receiver at a local or remote location. Hence, the wireless radio 640 can be any device capable of wireless communication and having a processor for performing specific programmed tasks/functions in order to determine the soil moisture level based on the conductivity between the electrodes. In another embodiment, a separate data processing device can be used (as shown and described with respect to the sensor 200 of FIG. 2).

A power source 699 powers the sensor 600. In an embodiment, for example, a battery and/or a solar panel can be used to power the sensor 600. A connector 666 (e.g., one or more wires, a bus, etc.) connects the power source 699 to the wireless radio 640 and the processor 650.

An enclosure 677, attached to the top of the double groove helical structure 610, includes the radio 640 (with processor 650), connector 666, portions of the connectors 631, 632, 633, 634, and possibly portions of the power source 699.

Figure 7:
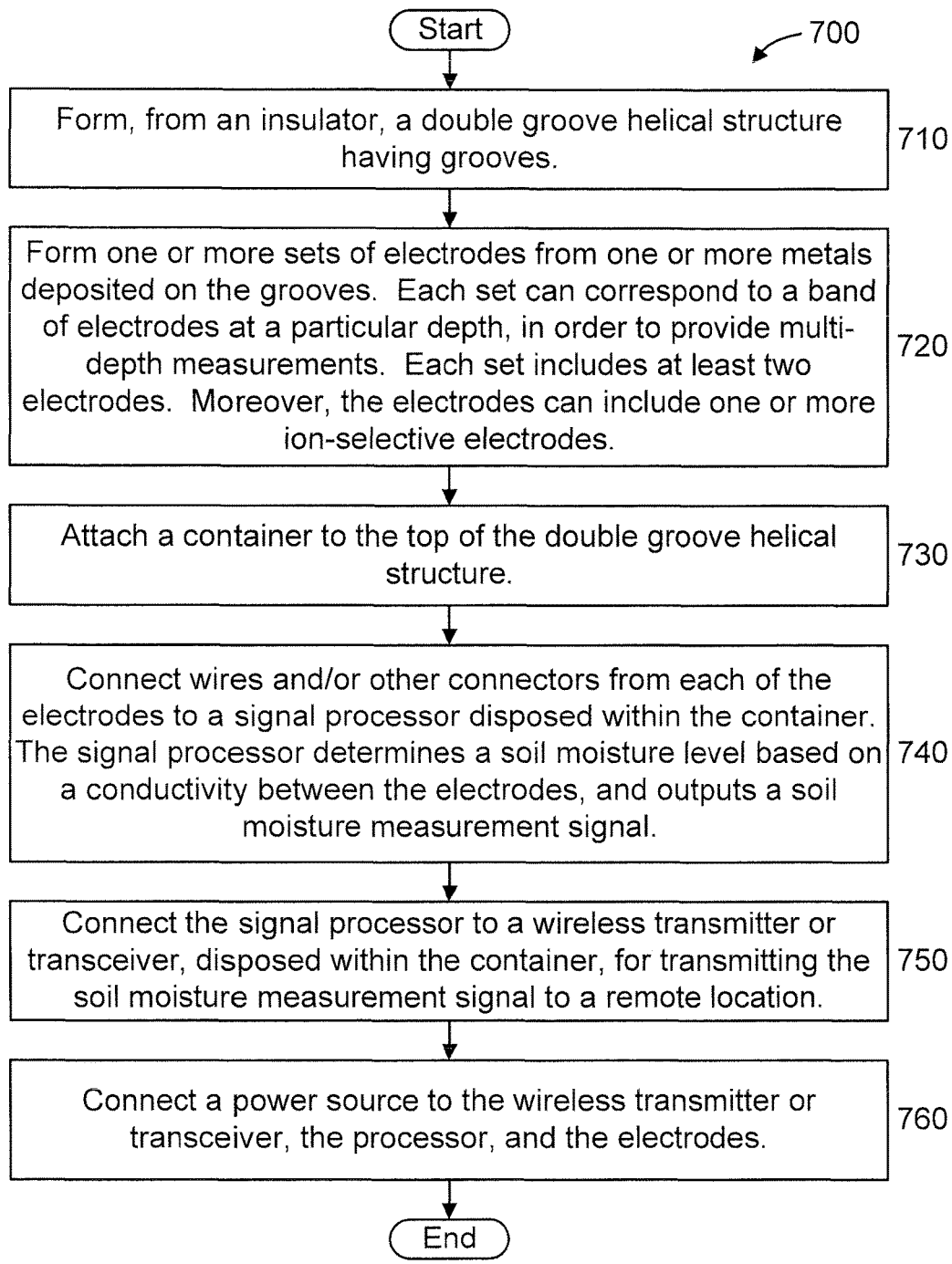
FIG. 7 shows an exemplary method 700 for forming a soil moisture sensor, in accordance with an embodiment of the present principles.

FIG. 7 shows an exemplary method 700 for forming a soil moisture sensor, in accordance with an embodiment of the present principles.

At step 710, form, from an insulator, a double groove helical structure having grooves. The insulator can be plastic, ceramic, or any insulating material.

At step 720, form one or more sets of electrodes from one or more metals deposited on the grooves. Each set can correspond to a band of electrodes at a particular depth, in order to provide multi-depth measurements. Each set includes at least two electrodes. Moreover, the electrodes can include one or more ion-selective electrodes.

At step 730, attach a container to the top of the double groove helical structure.

At step 740, connect wires and/or other connectors from each of the electrodes to a signal processor disposed within the container. The signal processor determines a soil moisture level based on a conductivity between the electrodes, and outputs a soil moisture measurement signal.

At step 750, connect the signal processor to a wireless transmitter or transceiver, disposed within the container, for transmitting the soil moisture measurement signal to a remote location.

At step 760, connect a power source to the wireless transmitter or transceiver, the processor, and the electrodes.

Figure 8:
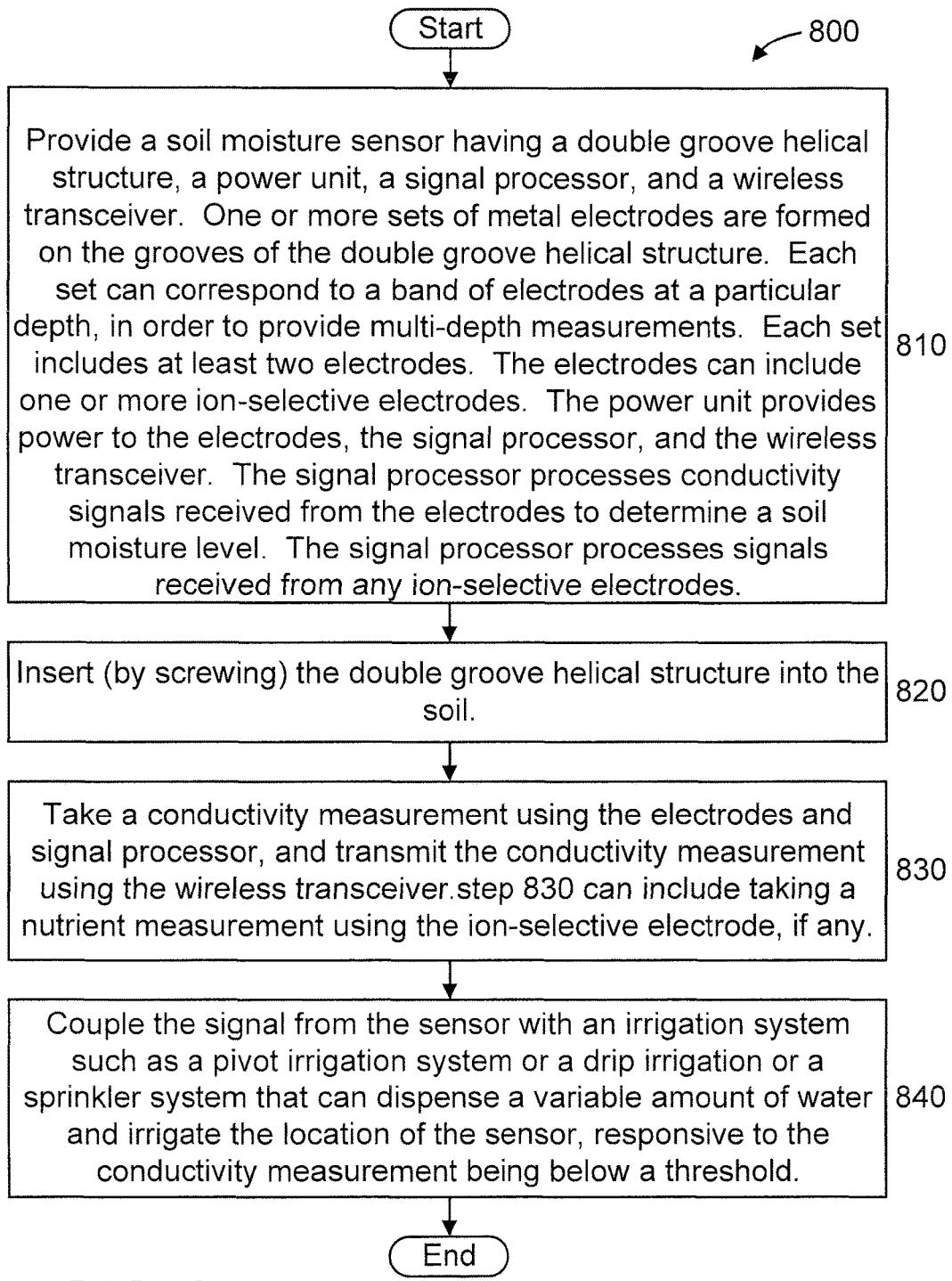
FIG. 8 shows an exemplary method 800 for soil moisture sensing, in accordance with an embodiment of the present principles.

FIG. 8 shows an exemplary method 800 for soil moisture sensing, in accordance with an embodiment of the present principles.

At step 810, provide a soil moisture sensor having a double groove helical structure, a power unit, a signal processor, and a wireless transceiver. One or more sets of metal electrodes are formed on the grooves of the double groove helical structure. Each set can correspond to a band of electrodes at a particular depth, in order to provide multi-depth measurements. Each set includes at least two electrodes. Moreover, the electrodes can include one or more ion-selective electrodes. The power unit provides power to the electrodes, the signal processor, and the wireless transceiver. The signal processor processes conductivity signals received from the electrodes to determine a soil moisture level. The signal processor can also process signals received from any ion-selective electrodes.

At step 820, insert (by screwing) the double groove helical structure into the soil.

At step 830, take a conductivity measurement using the electrodes and signal processor, and transmit the conductivity measurement using the wireless transceiver. In an embodiment, step 830 can include taking a nutrient measurement using the ion-selective electrode, if any. The resultant signal(s) can be combined with data from a variety of other sources like satellite measurements, topography or soil data to extract the moisture level in the soil. The calculations can reveal the spatial variation of the soil moisture level.

At step 840, couple the signal from the sensor with an irrigation system such as a pivot irrigation system or a drip irrigation or a sprinkler system that can dispense a variable amount of water and irrigate the location of the sensor, responsive to the conductivity measurement being below a threshold. Step 840 can involve activating an irrigation system.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A soil moisture sensor, comprising:
   a double groove helical structure having grooves and formed from an insulator, the grooves driving the soil moisture sensor into a ground portion perpendicular to a surface of the ground portion;
   at least a first electrode and a second electrode formed from one or more metals deposited at least two different locations on the grooves;
   a processor for processing a soil moisture measurement signal based on a conductivity between the electrodes; and
   a wireless transmitter for transmitting the soil moisture measurement signal to a remote location.

2. The soil moisture sensor of claim 1, further comprising a third electrode formed from the one or more metals or a different metal and deposited at a different location on the grooves than the first and second electrodes, wherein the third electrode is configured as a reference electrode for three electrode electrochemical measurements.

3. The soil moisture sensor of claim 1, further comprising a third and a fourth electrode formed from the one or more metals or one or more different metals and deposited at different locations than the first and second electrodes, wherein the third electrode and the fourth electrode are respectively configured as a reference electrode and a sense electrode for four electrode electrochemical measurements.

4. The soil moisture sensor of claim 1, wherein the electrodes are segmented to allow multi-electrode electrochemical measurements.

5. The soil moisture sensor of claim 1, further comprising a pair of ion-selective electrodes for measuring micronutrients in the soil.

6. The soil moisture sensor of claim 5, wherein the pair of ion-selective electrodes is deposited on at least a portion of at least one of the first electrode and the second electrode.

7. The soil moisture sensor of claim 1, wherein the insulator forming the double groove helical structure electrically isolates the electrodes from each other.

8. The soil moisture sensor of claim 1, wherein the insulator is a plastic or ceramic material.

9. The soil moisture sensor of claim 1, wherein the first and second electrodes form an electrode pair for soil moisture measurement at a given depth, and the sensor further comprises at least one other electrode pair for soil moisture measurement at at least one other given depth, to provide single-sensor, multi-depth soil moisture measurements.

10. The soil moisture sensor of claim 1, wherein the one or more metals comprise at least two different metals selected based on at least one of corrosion resistance and electrochemical potential.

11. A soil moisture sensing system, comprising:
a plurality of soil moisture sensors, each including:
 a double groove helical structure having grooves and formed from an insulator, the grooves driving the soil moisture sensor into a ground portion perpendicular to a surface of the ground portion;
 at least a first electrode and a second electrode formed from one or more metals deposited at least two different locations on the grooves;
 a processor for processing a soil moisture measurement signal based on a conductivity between the electrodes; and
 a wireless transmitter for transmitting the soil moisture measurement signal, and
 a wireless receiver for receiving the soil moisture measurement signal at a remote location.

12. The soil moisture sensing system of claim 11, wherein at least one of the plurality of soil moisture sensors further comprises a third electrode formed from the one or more metals or a different metal and deposited at a different location on the grooves than the first and second electrodes, wherein the third electrode is configured as a reference electrode for three electrode electrochemical measurements.

13. The soil moisture sensing system of claim 11, wherein at least one of the plurality of soil moisture sensors further comprises a third and a fourth electrode formed from the one or more metals or one or more different metals and deposited at different locations than the first and second electrodes, wherein the third electrode and the fourth electrode are respectively configured as a reference electrode and a sense electrode for four electrode electrochemical measurements.

14. The soil moisture sensing system of claim 11, wherein the electrodes of at least one of the plurality of soil moisture sensors are segmented to allow multi-electrode electrochemical measurements.

15. The soil moisture sensing system of claim 11, wherein at least one of the plurality of soil moisture sensors further comprises a pair of ion-selective electrodes for measuring micro-nutrients in the soil.

16. The soil moisture sensing system of claim 15, wherein the pair of ion-selective electrodes is deposited on at least a portion of at least one of the first electrode and the second electrode of the at least one of the plurality of soil moisture sensors.

17. The soil moisture sensing system of claim 11, wherein the insulator forming the double groove helical structure electrically isolates the electrodes on any given one of the plurality of soil moisture sensors from each other.

18. The soil moisture sensing system of claim 11, wherein the insulator is a plastic or ceramic material.

19. The soil moisture sensing system of claim 11, wherein the first and second electrodes form an electrode pair for soil moisture measurement at a given depth, and the sensor further comprises at least one other electrode pair for soil moisture measurement at at least one other given depth, to provide single-sensor, multi-depth soil moisture measurements for measuring a water propagation speed into the soil.

20. The soil moisture sensing system of claim 11, wherein the one or more metals comprise at least two different metals selected based on at least one of corrosion resistance and electrochemical potential.

* * * * *